US009228983B2

(12) United States Patent
Bailey et al.

(10) Patent No.: US 9,228,983 B2
(45) Date of Patent: Jan. 5, 2016

(54) PROCESS ANALYTIC DEVICE WITH IMPROVED THERMAL STABILITY

(71) Applicant: Rosemount Analytical Inc., Houston, TX (US)

(72) Inventors: Edward J. Bailey, Cypress, TX (US); Leighton M. Fields, Rosharon, TX (US)

(73) Assignee: Rosemount Analytical Inc., Houston, TX (US)

( * ) Notice: Subject to any disclaimer, the term of this patent is extended or adjusted under 35 U.S.C. 154(b) by 366 days.

(21) Appl. No.: 13/826,720

(22) Filed: Mar. 14, 2013

(65) Prior Publication Data
US 2014/0260532 A1     Sep. 18, 2014

(51) Int. Cl.
*G01N 30/30*    (2006.01)
*G01N 30/66*    (2006.01)
G01N 30/02    (2006.01)
G01N 30/72    (2006.01)
G01N 30/88    (2006.01)

(52) U.S. Cl.
CPC ............... *G01N 30/30* (2013.01); *G01N 30/66* (2013.01); *G01N 30/7206* (2013.01); *G01N 2030/025* (2013.01); *G01N 2030/3007* (2013.01); *G01N 2030/3046* (2013.01); *G01N 2030/8886* (2013.01)

(58) Field of Classification Search
CPC .. B01D 15/34; B01D 15/08; G01N 2030/025; G01N 30/02; G01N 2030/3046; G01N 30/7206; G01N 2030/3007; G01N 2030/3053; G01N 30/54
See application file for complete search history.

(56) References Cited

U.S. PATENT DOCUMENTS

| 3,828,184 | A | * | 8/1974 | Lupton | 250/304 |
| 4,096,908 | A | * | 6/1978 | Lamy | 165/64 |
| 5,043,576 | A | * | 8/1991 | Broadhurst et al. | 250/293 |
| 5,588,988 | A | * | 12/1996 | Gerstel et al. | 96/101 |
| 5,686,656 | A | * | 11/1997 | Amirav et al. | 73/23.41 |
| 5,756,878 | A | * | 5/1998 | Muto et al. | 73/25.03 |
| 5,778,681 | A | * | 7/1998 | Li et al. | 62/50.2 |
| 5,808,179 | A | | 9/1998 | Sittler et al. | |
| 5,954,860 | A | * | 9/1999 | Gordon | 95/87 |
| 6,054,683 | A | * | 4/2000 | Bremer et al. | 219/388 |
| 6,113,722 | A | * | 9/2000 | Hoffman et al. | 156/155 |
| 6,134,945 | A | * | 10/2000 | Gerstel et al. | 73/23.42 |
| 6,461,515 | B1 | * | 10/2002 | Safir et al. | 506/12 |
| 6,465,777 | B1 | * | 10/2002 | Rache | 250/287 |
| 6,907,796 | B2 | * | 6/2005 | Bremer et al. | 73/863.11 |

(Continued)

FOREIGN PATENT DOCUMENTS

CN      201314906 Y     9/2009
DE      3047601 A   *   7/1982

OTHER PUBLICATIONS

First Chinese Office Action for Application No. 201310254759.8, dated Apr. 3, 2015, 15 pages.

(Continued)

*Primary Examiner* — David A Rogers
(74) *Attorney, Agent, or Firm* — Christopher R. Christenson; Kelly, Holt & Christenson, PLLC

(57) ABSTRACT

A process analytic device has an input to receive a sample of interest. An analytic detector is operably coupled to receive the sample of interest and to provide an analytic output relative to the sample of interest. A heat pipe is thermally coupled to the analytic detector. In one embodiment, the process analytic device is a process gas chromatograph.

13 Claims, 2 Drawing Sheets

(56) References Cited

U.S. PATENT DOCUMENTS

| | | | |
|---|---|---|---|
| 8,378,293 B1* | 2/2013 | Quimby et al. | 250/282 |
| 8,726,747 B2* | 5/2014 | Kennett et al. | 73/864.51 |
| 2005/0268693 A1* | 12/2005 | Hasselbrink et al. | 73/23.42 |
| 2007/0107675 A1* | 5/2007 | Kurano | 122/408.1 |
| 2011/0107816 A1* | 5/2011 | Barth | 73/25.03 |
| 2011/0108568 A1* | 5/2011 | Hogan | 222/1 |
| 2012/0141345 A1* | 6/2012 | Slaten | 423/235 |
| 2012/0149125 A1* | 6/2012 | Earley et al. | 436/173 |
| 2012/0285223 A1* | 11/2012 | Andrews et al. | 73/61.53 |
| 2013/0071867 A1* | 3/2013 | Fadgen | 435/23 |
| 2013/0078609 A1* | 3/2013 | Tverskoy | 435/3 |
| 2013/0256523 A1* | 10/2013 | Steiner et al. | 250/282 |
| 2015/0013430 A1 | 1/2015 | Black et al. | |

OTHER PUBLICATIONS

Second Office Action from Chinese Application No. 201310254759.8, from Oct. 9, 2015, 7 pages.

* cited by examiner

PROCESS ANALYTIC DEVICE WITH IMPROVED THERMAL STABILITY

BACKGROUND

Analytical devices and instruments are used in a number of applications to quantitatively and/or qualitatively analyze a sample of interest. Analytical devices and instruments are often found in laboratories and are sometimes employed within processing operations. As used herein, an analytical device is any device, system or arrangement that is able to receive a sample of interest and provide an indication of some aspect of the sample of interest. Analytical devices include, without limitation, process gas analyzers, NO/NOx analyzers, hydrocarbon analyzers, continuous emission monitoring systems and process gas chromatographs.

Gas chromatographs (GC) rely on precise control of temperature of chromatographic columns, detectors, and support systems. One or more electrical heaters are used to heat a controlled oven, chamber or locally heated zone or substrate (hereinafter oven). Such heaters operate by cycling on/off in a closed loop control system with temperature feedback provided by one or more temperature sensors in or near the oven. Such state of the art oven temperature control systems provide adequate control of a temperature set point (typically +/−0.1° C. or less) for the oven when external ambient conditions are stable. However, it is common for process gas chromatographs to be installed without protection from the ambient environment. Such exposed process gas chromatographs may experience ambient temperature variations from −40° to +60° C. but are still expected to deliver consistent measurement performance across such wide ambient variations.

As the art of process analytic devices has progressed, there is increasing pressure to provide a more precise analytic output even when faced with significant ambient temperature fluctuations.

SUMMARY

A process analytic device has an input to receive a sample of interest. An analytic detector is operably coupled to receive the sample of interest and to provide an analytic output relative to the sample of interest. A heat pipe is thermally coupled to the analytic detector.

DETAILED DESCRIPTION OF ILLUSTRATIVE EMBODIMENTS

Figure 1:
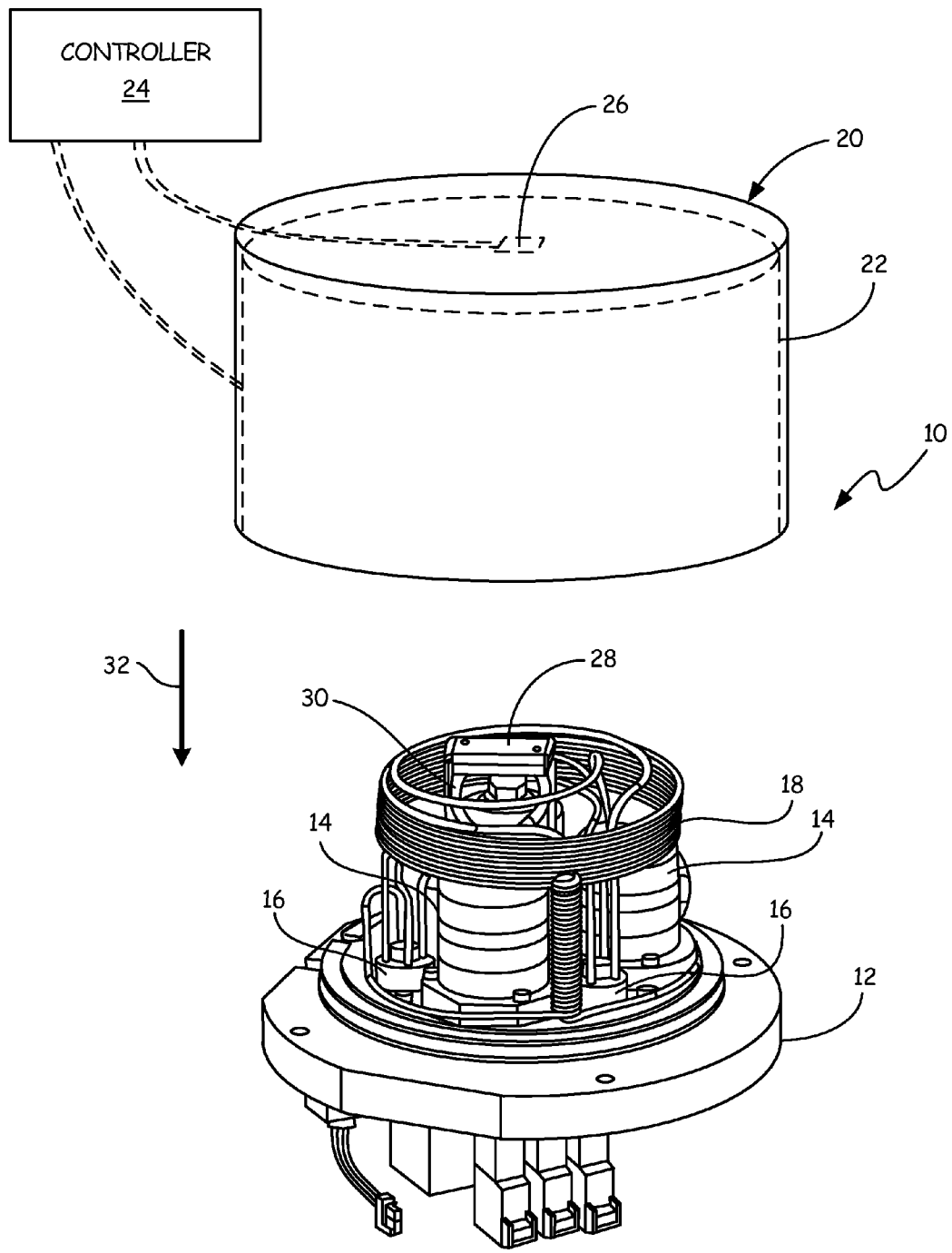
FIG. 1 is a diagrammatic view of a portion of a process gas chromatograph in accordance with an embodiment of the present invention.

In current state of the art gas chromatographs, an oven heater controls an average oven temperature driven by one or more measurements from temperature sensors within the oven. Examples of such sensors include thermocouples, resistance temperature devices (RTD's) and thermistors. Commonly, a single temperature sensor is used. The single point measurement leads to performance compromises when heat losses from the oven occur as a result of external ambient temperature variations. Typically, as the oven loses heat, there is a lag time before the control sensor indicates to the control system that the average oven temperature has dropped and the control system responds by applying power to the heater(s). The result is that some oven surfaces or areas may have cooled below the control set point before heating is commanded by the control system and that other areas of the oven will achieve temperatures higher than the set point before the control system senses that enough heat has been added to the oven to achieve the set point. Thus, significant variations may occur in current chromatograph ovens as a result of ambient influences.

Thermal Conductivity Detectors (TCD's) are commonly used in gas chromatographs and function by measuring minute deviations in thermal conductivity of gases flowing through the detector. Such detectors are extremely sensitive to temperature variations; affecting measurement stability and precision. Generally, the location of a TCD in the chromatograph oven is not thermally symmetrical. As the oven control system and heater(s) respond to external influences, localized temperature variations occur within the oven as described above. These oven variations allow for thermal losses or gains through the TCD mount and/or TCD body to cause the localized temperature of the TCD body to vary as a result. Any such temperature deviation of the TCD itself results in measurement variation.

Embodiments of present invention provide for improved measurement performance of temperature sensitive detectors within a process analytic device by significantly improving thermal control relative to such detectors. Embodiments of the present invention generally employ one or more heat pipes to provide additional heating to the TCD body to counteract thermal losses and reduce the effect of thermal variations within the oven.

A heat pipe is generally formed as conduit constructed from of a relatively high thermal conductivity metal, such as copper. The conduit is generally evacuated and then provided with working fluid after which the conduit is sealed. Examples of working fluids include water, ethanol, and acetone. The working fluid is selected such that when it contacts the hot (evaporator) side of the heat pipe it absorbs heat and turns into vapor. The vapor then flows to the cold side where it releases thermal energy (cools) and condenses back to a liquid. The liquid then returns to the hot side via a capillary action or gravity and the process repeats.

Heat pipes are known and used for conducting heat from the hot (evaporator) to the cold (condenser) zone. Heat pipes are commonly used to remove waste heat (e.g. cooling a microprocessor), or drive heat into a device from a remote heater. Heat pipe technology typically provides thermal conductivities 100-200 times that of copper. Heat pipe performance is such that significant heat flux can be moved across a small deviation in temperature between the evaporator and the condenser.

Embodiments of the present invention generally employ one or more heat pipes arranged in a manner that couple the thermal conductivity detector body with the temperature-controlled oven. A heat pipe is generally a passive device that provides a high level of thermal coupling between its evaporator and its condenser. One embodiment of the present invention locates the heat pipe evaporator such that it extends into the precisely controlled oven with the heat pipe condenser located on or proximate the thermal conductivity detector itself. This arrangement provides a very stable heat source to add supplemental heating (or cooling) to the thermal conductivity detector based on the temperature of the heat pipe evaporator, without the need to have any additional control system to control heat pipe operation. The heat pipe evaporator is ideally located in the area of the oven determined to be most precisely thermally controlled and most immune to external thermal influences; typically near the temperature sensor of the thermal control system for the oven. Thus, the heat source for the heat pipe is exceptionally stable and provides more precise control than a modulated supplemental heater. This stable passive heat source pumps heat from the most stable area of the oven to the thermal conductivity detector body. This, in turn, helps compensate for heat demand variation induced by external influences. Sourcing the heat from the most isothermal area of the oven provides supplemental heating to the thermal conductivity detector body at a constant temperature providing less actual deviation in practice than the oven control provides for. This arrangement eliminates the need for a supplemental heater and controller and/or additional insulation or thermal conductivity detector isolations. This steady state source of supplemental heat minimizes variation of the thermal conductivity detector body and thus provides for improved measurement performance in a varying environment.

FIG. 1 is a diagrammatic perspective view of a portion of a process gas chromatograph 10 in accordance with an embodiment of the present invention. FIG. 1 illustrates a portion of an upper, thermally-controlled portion of process gas chromatograph 10. Specifically, chromatograph 10 includes base plate 12 which is preferably formed of a metal, such as aluminum or stainless steel. A plurality of multi-port flow valves 14 are mounted on base plate 12, along with a plurality of multi-port distribution fittings 16. Additionally, one or more suitable detectors for the process gas chromatograph, such as thermal conductivity detector 34 (shown in FIG. 2), are also mounted on or proximate base plate 12. One or more chromatographic separation columns are typically mounted proximate the various flow devices within an environmentally-sealed cover 20. A sample shut-off valve (not shown) which cuts off flow of sample gas during certain valve actuation configurations may be mounted within proximity of the other flow devices.

Within cover 20, one or more heaters 22 maintain precise thermal control of the entire assembly 10. For example, for process gas chromatography, the entire assembly 10 is typically maintained at approximately 80° C. plus or minus a fraction of a degree C. Heaters 22 are coupled to a controller 24 that may be a component of the process gas chromatograph 10 or separate. Controller 24 is also coupled to one or more temperature sensors 26 in order to determine the temperature within cover 20. Controller 24 selectively applies power to heaters 22 based on the measured temperature in order to provide precise thermal control within cover 20. This precise thermal control allows controller 24 to maintain the temperature of the sample of interest and the analytic detector at a specified temperature. However, as set forth above, it is possible for small thermal fluctuations to occur based on heat flow, time lag, and the control regime.

As shown in FIG. 1, a protective metal shield 28 is provided around heat pipe 30. When cover 20 is moved in the direction indicated by arrow 32 and mounted or otherwise affixed to process gas chromatograph 10, heaters 22 substantially encircle columns 18, valves, 14 and fittings 16. Additionally, temperature sensor 26, mounted to or within cover 20, is thermally coupled to metal shield 28. Shield 28, being metal, has a relatively high thermal conductivity and ensures that heat pipe 30 is in close thermal contact with temperature sensor 26.

Figure 2:
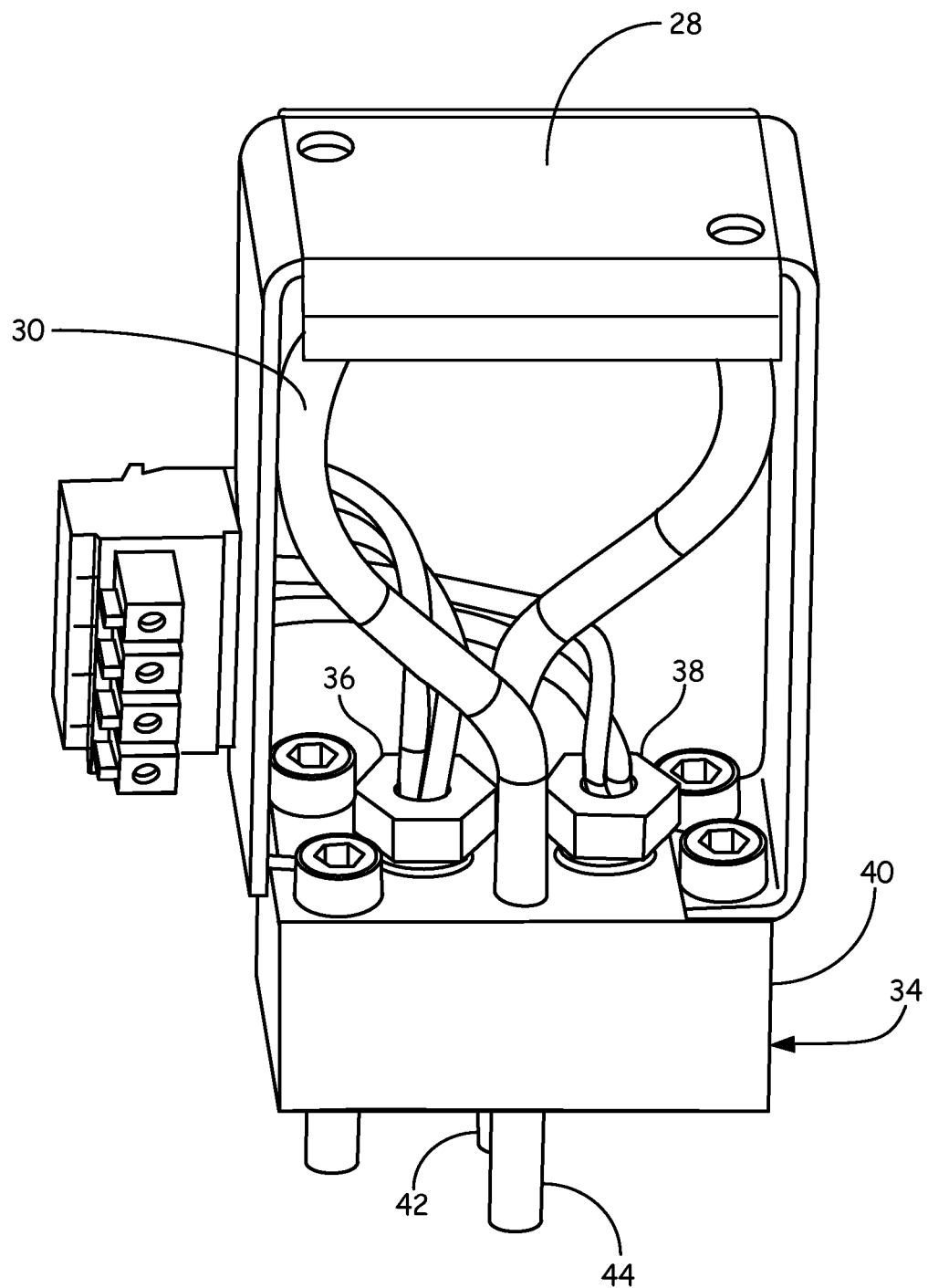
FIG. 2 is a diagrammatic perspective view of a thermal conductivity detector of a process gas chromatograph coupled to a heat pipe in accordance with an embodiment of the present invention.

FIG. 2 is a diagrammatic perspective view of a thermal conductivity detector of a process gas chromatograph coupled to a heat pipe in accordance with an embodiment of the present invention. Thermal conductivity detector 34 includes a pair of thermal conductivity sensors 36, 38 mounted within metal block 40. Sensors 36, 38 sense thermal conductivity of a reference gas and a sample of interest flowing through block 40 in order to provide an indication of thermal conductivity relative to a reference gas and a sample of interest. Sensors 36, 38 are coupled to measurement circuitry (not shown) in the process gas chromatograph such that the thermal conductivities can be processed to provide the analytic output. Heat pipe 30 includes two condensing ends 42, 44. Ends 42, 44 pass through block 40 and regions of heat pipe 30 near ends 42, 44 are in direct thermal contact with block 40. Additionally, as indicated in FIG. 2, the arrangement of sensors 36, 38 and the portions of heat pipe 30 passing through block 40 are preferably symmetrical such that heat flow is substantially identical for one sensor 36, 38 relative to the other sensor 38, 36.

Heat pipe 30 is preferably constructed from tubing formed of a metal with high thermal conductivity such as copper or aluminum. Additionally, given the precise nature of thermal control around 80° C., it is preferred that the working fluid of the heat pipe have a boiling point close to that value. One suitable example of a working fluid with a boiling point, at standard pressure, near 80° is ethanol. However, water can also be a suitable working fluid for an 80° C. control point if the pressure inside the heat pipe is reduced sufficiently. In at least some embodiments, it is also preferred that the entire assembly illustrated in FIGS. 1 and 2 be operated upside down such that the condensing ends 42, 44 of heat pipe 30 are above the evaporating loop coupled to shield 28. In this way, gravity will also assist with the return of condensate down from ends 42, 44 to the evaporative loop portion proximate shield 28.

Although the present invention has been described with reference to preferred embodiments, workers skilled in the art will recognize that changes may be made in form and detail without departing from the spirit and scope of the invention.

What is claimed is:

1. A process analytic device comprising:
   an input to receive a sample of interest;
   an analytic detector operably coupled to receive the sample of interest and to provide an analytic output relative to the sample of interest;
   a cover at least partially defining a heated chamber, and wherein the sample of interest flows into the heated chamber; and
   a heat pipe thermally coupled to the analytical detector, wherein an evaporative portion of the heat pipe is thermally coupled to the cover.

2. The process analytic device of claim 1, wherein the process analytic device is a process gas chromatograph.

3. The process analytic device of claim 1, wherein the analytic detector is disposed within the heated chamber.

4. The process analytic device of claim 1, wherein the evaporative portion of the heat pipe is thermally coupled to a temperature sensor.

5. The process analytic device of claim 1, wherein a condensing end of the heat pipe is in thermal contact with the analytical detector.

6. The process analytic device of claim 5, wherein the analytical detector is a thermal conductivity detector.

7. The process analytic device of claim 1, wherein a condensing end of the heat pipe is in thermal contact with the analytic detector.

8. The process analytic device of claim 1, wherein the heat pipe contains a working fluid with a boiling point of 80° C.

9. The process analytic device of claim 8, wherein the working fluid is water.

10. The process analytic device of claim 1, and further comprising a metallic shield disposed to protect the heat pipe.

11. The process analytic device of claim 1, and further comprising:
- at least one heater configured to heat the sample of interest and the analytic detector;
- a temperature sensor configured to provide an indication of temperature relative to the sample of interest or the analytic detector; and
- a controller coupled to the at least one heater and the temperature sensor to maintain the temperature of the sample of interest and the analytic detector at a specified temperature.

12. The process analytic device of claim 11, wherein the heat pipe has a working fluid therein having a boiling point at the specified temperature.

13. The process analytic device of claim 12, wherein the heat pipe has a first portion coupled to the analytic detector and a second portion thermally coupled to the temperature sensor.

* * * * *